(12) United States Patent
Pisanello et al.

(10) Patent No.: US 10,398,293 B2
(45) Date of Patent: Sep. 3, 2019

(54) OPTOGENETIC TOOL FOR MULTIPLE AND INDEPENDENTLY ADDRESSING OF PATTERNED OPTICAL WINDOWS

(71) Applicants: FONDAZIONE INSTITUTO ITALIANO DI TECNOLOGIA, Genoa (IT); PRESIDENT AND FELLOWS OF HARVARD COLLEGE, Cambridge, MA (US)

(72) Inventors: Ferruccio Pisanello, Lecce (IT); Luigi Martiradonna, London (GB); Leonardo Sileo, Calimera (IT); Ian Anton Oldenburg, Lexington, MA (US); Marco Pisanello, Felline di Alliste (IT); Bernardo Luis Sabatini, Newton, MA (US); John Abraham Assad, Brookline, MA (US); Massimo De Vittorio, Lecce (IT)

(73) Assignees: Fondazione Istituto Italiano di Tecnologia, Genoa (IT); President and Fellows of Harvard College, Cambridge, MA (US)

(*) Notice: Subject to any disclaimer, the term of this patent is extended or adjusted under 35 U.S.C. 154(b) by 759 days.

(21) Appl. No.: 14/905,374

(22) PCT Filed: Jul. 16, 2014

(86) PCT No.: PCT/IB2014/063147
§ 371 (c)(1),
(2) Date: Jan. 15, 2016

(87) PCT Pub. No.: WO2015/008233
PCT Pub. Date: Jan. 22, 2015

(65) Prior Publication Data
US 2016/0157706 A1 Jun. 9, 2016

(30) Foreign Application Priority Data

Jul. 17, 2013 (IT) .............................. TO2013A0603

(51) Int. Cl.
*A61B 1/07* (2006.01)
*A61B 5/00* (2006.01)
(Continued)

(52) U.S. Cl.
CPC .............. *A61B 1/07* (2013.01); *A61B 5/0084* (2013.01); *A61B 18/22* (2013.01); *A61N 5/062* (2013.01);
(Continued)

(58) Field of Classification Search
CPC ......... A61B 1/07; A61B 18/22; A61B 5/0084; A61B 2018/2261; A61B 2562/0233;
(Continued)

(56) References Cited

U.S. PATENT DOCUMENTS

| | | | | |
|---|---|---|---|---|
| 2007/0224264 A1* | 9/2007 | Antipov | ............... | A61K 9/0009 424/463 |
| 2013/0030274 A1* | 1/2013 | Jamieson | ............. | A61B 5/6848 600/377 |
| 2017/0326382 A1* | 11/2017 | Seymour | .............. | A61B 5/0084 |

FOREIGN PATENT DOCUMENTS

| | | |
|---|---|---|
| WO | 2009070160 A1 | 6/2009 |
| WO | 2011057137 A1 | 5/2011 |

OTHER PUBLICATIONS

Novotny, Lukas Hecht, Bert. (2006). Principles of Nano-Optics—6 Near-field optical probes. pp. 173-224 Cambridge University Press. Retrieved from https://app.knovel.com/hotlink/pdf/id:kt0084MDY1/principles-nano-optics/dielectric-probes.*

(Continued)

*Primary Examiner* — Christopher Koharski
*Assistant Examiner* — James Moss
(74) *Attorney, Agent, or Firm* — Arent Fox LLP; Michael Fainberg

(57) ABSTRACT

A multi-point light-delivering device, comprising a waveguide carrying light along a longitudinal axis and including multiple optical windows, through which the carried light is out-coupled from the waveguide. The waveguide comprises a tapered region along which the optical windows are distributed, wherein each optical window out-couples a specific subset of propagating modes of the carried light, to which the optical window is matched.

12 Claims, 4 Drawing Sheets

(51) Int. Cl.
    *G02B 6/26*     (2006.01)
    *A61B 18/22*     (2006.01)
    *A61N 5/06*     (2006.01)
    *G02B 6/14*     (2006.01)

(52) U.S. Cl.
    CPC .............. *A61N 5/0622* (2013.01); *G02B 6/14* (2013.01); *G02B 6/262* (2013.01); *A61B 2018/2255* (2013.01); *A61B 2018/2261* (2013.01); *A61B 2562/0233* (2013.01); *A61N 2005/063* (2013.01)

(58) Field of Classification Search
    CPC ................. A61N 5/0622; A61N 5/062; A61N 2005/063; G02B 6/14; G02B 6/262
    See application file for complete search history.

(56) References Cited

OTHER PUBLICATIONS

Zorzos et al. (Optics Letters, vol. 15, pp. 4133-4135, 2010; Optics Letters, vol. 37, pp. 4841-4843, 2012).*

Zorzos, A.N., Boyden, E.S., and Fonstad, C.G. (2010). Multiwaveguide implantable probe for light delivery to sets of distributed brain targets. Opt. Lett. 35, 4133-4135.*

Stark et al. (Journal of Neurophysiology, vol. 108, pp. 349-363, 2012).*

International Search Report dated Nov. 5, 2014.

Polina Anikeeva et al. "Optetrode: a multichannel readout for optogenetic control in freely moving mice", Nature Neuroscience, vl. 15, No. 1, Jan. 2012 pp. 163-172.

Wang et al. "Integrated device for combined optical neuromodulation and electrical recording for chronic in vivo applications", Journal of Neural Engineering, 9 (2012) pp. 1-14.

Zhang et al. "Integrated device for optical stimulation and spatiotemporal electrical recording of neural activity in light-sensitized brain tissue", Journal of Neural Engineering, 6 (2009) pp. 1-13.

Sébastien Royer et al. "Multi-array silicon probes with integrated optical fibers:light-assisted perturbation and recording of local neuralcircuits in the behaving animal" , European Journal of Neueroscience, vol. 31 pp. 2279-2291, 2010.

Anthony N. Zorzos et al. "A Multi-Waveguide Implantable Probe for Light Delivery to Sets of Distributed Brain Targets", Opt. Lett Dec. 15, 2010; 35 (24) 4133-4135.

Anthony N. Zorzos et al. "Three-dimensional multiwaveguide probe array for light delivery to distributed brain circuits", Dec. 1, 2012, vol. 37, No. 23 Optics Letters 4841-4843.

Eran Stark et al. "Diode probes for spatiotemporal optical control of multiple neurons in freely moving animals", J Neurophysiol 108: 349-363, 2012.

Sunil K. Khijwania et al."Effect of Launching Condition on Modal Power Characteristics of Multi-Mode Step-Index Optical Fiber: A Theoretical and Experimental Investigation" Fiber and Integrated Optics, 29: 62-75, 2010.

* cited by examiner (a) Realization of the device (c) Photostimulated neural activity at θ = 8°

(b) Photostimulated neural activity at θ = 3°

OPTOGENETIC TOOL FOR MULTIPLE AND INDEPENDENTLY ADDRESSING OF PATTERNED OPTICAL WINDOWS

STATEMENT AS TO RIGHTS TO INVENTIONS MADE UNDER FEDERALLY SPONSORED RESEARCH OR DEVELOPMENT

This research was made, in part, with government support under NIH Grants R01 NSO46579 and F31 MH093026 awarded by the National Institutes of Health; the United States Government has certain rights in the invention.

BACKGROUND

The present invention relates to a multi-point light-delivering device, comprising a waveguide carrying light along a longitudinal axis and including multiple optical windows, through Which the carried light is out-coupled from the waveguide.

Such a device may be used as an optogenetic tool to be exploited both for in-vitro experiments with neuronal tissues and for in-vivo experiments or medical applications, in such experiments, specific neurons are targeted to express light-sensitive proteins or are exposed to light-sensitive compounds. Examples of light-sensitive proteins include proteins that alter the electrical and biochemical state of the neuron or that activate or repress specific enzymes. Light-sensitive compounds include small molecules that when exposed to light release an active compound such as a neurotransmitter, second messenger, or neuromodulator. Thus the electrical, biochemical, and signalling state of a neuron can be regulated by optical stimulation, typically in the visible spectral range or in the near infrared. The main advantage of optical stimulation compared to classical electrical or pharmacological stimulation is the possibility to selectively activate or inactivate (one or more) genetically defined set(s) of neurons with high temporal and spatial precision. This can be achieved by genetic approaches that can provide specific neurons with light-sensitive proteins while leaving neighbouring cells insensitive. In contrast, electrical or pharmacological stimulation generally affects all cells located near the electrode tip, with no cellular precision.

Optical stimulation in brain tissue is often performed simultaneously with electrical recording of the triggered neuronal activity. In in-vivo experiments, common optogenetic tools are optical fibers used to shine visible light inside the brain, combined with single- or multi-electrode recording systems (single microwires, tetrodes, multielectrode arrays fabricated on silicon shafts, etc.) for the electrical readout. These tools are managed separately, and neural responses can be monitored near and far from the optical stimulation region. In recent years, fully integrated devices combining optical modulation and electrical recording in a single implantable tool have been developed, thus improving compactness and reducing surgical intervention steps.

To understand the behaviour of complex neural circuits and to increase the amount of data collected in single experiments, multiple-channel recording is crucial. However, in standard devices light is delivered into the brain by means of a single optical fiber able to deliver light only to a single, fixed area of the brain. The high number of recording channels is thus not accompanied by comparable amount of light delivery points, creating a mismatch in which electrical activity can be detected with high spatial resolution, while the optical excitation has a poor spatial selectivity. The possibility to dynamically select the excited area in real time would boost the performances of currently available devices, allowing more flexible and powerful causal manipulation of neural circuits.

Recently, integrated single optical excitation/multiple electrical readout systems have been reported in Anikeeva et al. (Nature Neuroscience, vol. 15, pp. 163-170, 2012, doi: 10.10381/nn.2992) and Wang et al. (Journal of Neural Engineering, vol. 9, p. 016001, 2012, doi: 10.1088/1741-2560/9/016001). In Anikeeva et al., a single multimodal fiber is used to convey light, while four tetrodes are glued on its sides and extended 300 µm or more beyond the tip of the optical fiber to record electrical signal from illuminated brain regions. The system is compact and lightweight, suitable for chronic implantation on freely moving animals. However, this layout limits localization of the recording sites to a small brain region near the tip of the fiber, with the effective distance determined by the light intensity. The absorption and scattering of light in brain tissue leads to a decrease in light intensity as a function of distance from the fiber tip: electrode tips closer than 200-300 µm from the fiber tip will suffer from high Photoelectric noise, while sensors farther than 1000 µm will generally be outside of the range of light illumination. The effective region will be therefore limited to few hundreds microns from the fiber tip.

The second approach proposes a tapered optical fiber positioned at the center of a two-dimensional microelectrode array consisting of 30 microfabricated silicon tips for electrical recording. The optical fiber is tapered only for the purpose of preventing tissue damages. The fiber can also be covered by a metallic layer to provide an additional electrical recording site (see also Zhang et al, Journal of Neural Engineering, Vol. 6, p. 055007, 2009, doi: 10.1088/1741-2560/6/5/055007). Inter-electrode distance and minimum electrode-fiber distance is determined by the microfabrication (in the proposed device, it is 400 µm). Light intensity is adjusted to excite neurons from the tip of the fiber to the closer electrodes of the array. The excited brain volume can again he expanded by increasing the emitted optical power, but increasing light intensity to reach distant recording sites will lead to increased electrical artifacts on the closer sites.

Commercially available optrodes (NeuroNexus) also combine a linear array of recording sites fabricated on a single silicon shaft with a hare optical fiber collinearly mounted on top of the array (see also Royer at al., European Journal of Neuroscience, Vol. 31, pp. 2279-2291, 2010, doi: 10.1111/j.1460-9568.2010.07250.x). Again, the electrodes/fiber tip distance is determined by the light intensity: closer distances require lower optical power to avoid photoelectric noise; therefore reduced brain volumes are excited. Typically, intermediate fiber distances of 200 µm from the closest pad are provided as a commercial standard.

It is therefore evident that optrodes based on a single light-emitting point source have significant limitations for the integration of multiple-site recording systems. Multi-point light delivery has been proposed. by Zorzos et al. (Optics Letters, Vol. 15, pp. 4133-4135, 2010; Optics Letters, Vol. 37, pp. 4841-4843, 2012) and Stark et al. (Journal of Neurophysiology, vol. 108, pp. 349-363, 2012). The approaches of Zorzos et al. comprise a parallel array of optical waveguides having a 45° terminal cut covered by aluminium, so that 90° light emission, perpendicular to the probe axis, is obtained. Each waveguide can be separately coupled to different light sources or to the same laser source shared by all the waveguides by moans of micro-mirror devices, therefore obtaining separate optical stimulation points in two- and three-dimensional environments.

Although electrical recording is not described in these publications, integration with silicon shafts and multiple recording sites is suggested. Stark et al. also propose the use of multiple diode-fiber assemblies, where each single-core optical fiber is glued to a different silicon shaft with single or multiple recording sites. In this case, each fiber is independently excited and multiple wavelengths and light powers can be used. Both strategies allow an improved distribution of light intensity in the investigated brain volume, but this is obtained by recurring to multiple light sources and complicated and cumbersome coupling strategies.

WO 2011/057137 discloses a waveguide neural interface device able to target different brain regions. It is based on the combination of sonic of the above described works and it covers a wide area of possible device configurations. In particular, light directing elements are provided on waveguides and/or on optical fibers in order to redirect light away for the longitudinal axis of the waveguide. These elements allow the illumination of specific zones of the tissue surrounding the device and, as stated by the inventors, can be "one or more of several variations, including one or more features that refract, reflect, focus, and/or scatters light, and/or perform any suitable manipulation of light". That is, light is redirected and/or manipulated by means of light-directing elements realized on a waveguide, while the purpose of the waveguide is just to carry light to the reflecting elements. According to WO 2011/057137, the waveguide could he tapered to reduce tissue damages.

The device configuration disclosed by WO 2011/057137 may he somewhat complex and cumbersome, particularly when a great number of light-directing elements must be provided with the waveguide.

One object of the invention is therefore to provide a multi-point light-delivering device that overcomes the drawbacks of existing devices,

SUMMARY

In accordance with this object, the invention proposes a device of the type defined at the beginning, wherein said waveguide comprises a tapered region along which said optical windows arc distributed, and wherein each optical window out-couples a specific subset of propagating modes of the carried light, to which said optical window is matched.

The light-delivering device according to the invention is based on a modal-demultiplexing principle founded on the modal selectivity of a tapered optical fiber. The purpose of the taper is to select and modify the modes injected into the distal end of the fiber, while the optical apertures realized on the tapered region define the points at which subsets of propagating modes can out-couple in the surrounding environment. As a consequence, in the present invention a single fiber can be exploited to independently address light to multiple optical windows, manipulating light mainly by means of the waveguide itself and not by light-directing elements. This feature is of paramount importance when small size and simplicity of construction are desired, as for example in optogenetic experiments and applications.

Further advantages of the device according to the invention are:
- independent addressability of the optical windows, even if a single optical fiber is used;
- minimized invasiveness while keeping the multi-point emitting behavior;
- minimized photoelectrical noise when electrodes and light emitting elements are realized on the same or on adjacent shafts (reduced impact of the Becquerel effect on signals obtained through the neural interface device and improved accuracy of data collection in the neural interface device);
- minimization of wiring requirements.

BRIEF DESCRIPTION OF THE DRAWINGS

Further characteristics and advantages of the proposed device will be presented in the following detailed description, which refers to the attached drawings, provided purely by way of non-limiting example, in which.

DETAILED DESCRIPTION

Figure 1:
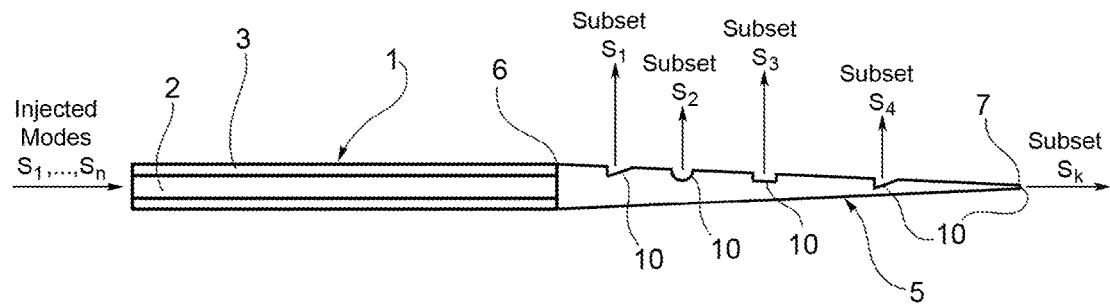
FIG. 1 is a schematic, cross-sectional view illustrating a multi-point light-delivering device according to the invention.

With reference to FIG. 1, a multi-point light delivering device according to the invention is shown. This device comprises a waveguide 1, a section of which is shown in FIG. 1. This waveguide is an optical fiber conventionally comprising a core 2 and a cladding 3. The waveguide 1 extends along a longitudinal axis, between a distal end (not shown in FIG. 1), which is adapted to be coupled to a light source, and a proximal end 5. Light injected by the light source is carried by the waveguide 1 along its longitudinal axis, and out-coupled by the proximal end 5 of the waveguide 1. The proximal end 5 is as tapered region of the waveguide 1, extending between a taper base 6 adjacent to the rest of the waveguide 1, and a taper tip 7. This tapered region has preferably a taper angle between 1° and 10°, preferably between 3° and 6°. The tapered region 5 of the waveguide is coated with a reflective coating. A plurality of optical windows 10 are formed along the tapered region 5.

The device of FIG. 1 may be used as an optogenetic tool able to selectively and dynamically target different regions of neuronal tissues or any optical sensitive material or environment. It is based on the modal selectivity of a micro-structured and tapered optical fiber, which radiate in the surrounding tissue only defined subsets of propagating modes by means of properly designed optical windows.

A certain set of propagating modes $\{s_1, \ldots, s_N\}$ is injected into the optical fiber 1 by means of an external light source. These modes propagate up to the tapered region 5 covered with a highly reflective material. When entering the taper, each mode undergoes a modal manipulation and selection process because the taper no longer supports all the modes allowed in the straight core-cladding fiber 1. In particular, the lower the diameter of the taper, the lower the number of modes propagating toward the taper tip 7. In order to allow out-coupling of the propagating modes into the surrounding environment, optical windows 10 are realized along the taper and/or on its tip. Each optical window 10 essentially comprises a recess formed on the outer surface of the tapered region, and is obtained by removing part of the reflective coating or by partially piercing also the taper, depending on the application. In general, an optical window can be any system able to out-couple some of the guided modes in the surrounding environment. Indeed, optical strategies already presented in literature can be also implemented on or inside each single window to define the out-coupled modal subset. As an example, one, two or three-dimensional photonic crystal structures, nanostructured metamaterials or plasmonic antennas/resonators can be created next to the optical window.

A key feature of the proposed approach is that the i-th window out-couples only a subset of the guided modes $S_i = \{s_m, \ldots, s_n, \ldots, s_g\}$ to which it is matched, while the remaining radiation still undergoes to the modal selection made by the taper. The number and type of out-coupled modes at each window 10, as well as the out-coupling efficiency of the subset, depend on several structural parameters of the device and of the window itself, including:

Core/cladding size and numerical aperture of the fiber 1;
Taper region 5 angle and length;
Shape, lateral dimensions and depth of the window 10;
Distance of the windows 10 from the base of the taper 6.

By engineering these parameters, the structure can be designed in order to obtain the out-coupling of a specific modal subset predominantly from one window 10. This creates a modal-demultiplexer based on the fiber's taper. As a consequence, by injecting into the core-cladding section of the fiber 1 only the modal subset $S_i$, radiation in the surrounding environment will be obtained predominantly from the i-th window. As well, if injection is switched between the subsets $S_i$ and $S_j$, radiation will switch between the i-th and j-th windows, thus allowing the dynamic delivery of light in two different regions of the tissue surrounding the taper. Dynamic switching among different light points using a single fiber instead of multiple waveguides allows a single light source to be coupled to the system, thus simplifying the injection requirements. Moreover, the injection of defined modal subsets at the fiber input can be obtained with very simple optical solutions mainly based on geometrical-optic considerations. It is worth noting that this strategy still allows the use of different wavelengths at the same time to stimulate and/or inhibit neuronal activity.

The ability to control the modal behavior of the out-coupled light allows good control of the radiation direction, enabling perpendicular and/or parallel emission (i.e., emission through the side windows and/or the tip window, respectively) with respect to the waveguide axis, according to the brain volumes to be investigated. Controlling the shape and position of the optical windows according to the working wavelength can also he exploited to create interference fringes.

Figure 2:
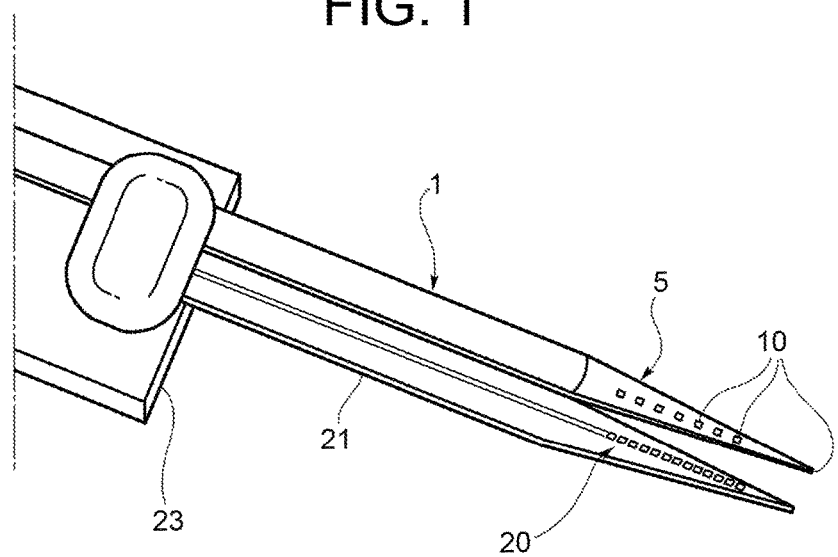
FIG. 2 is a perspective view illustrating an optogenetic tool incorporating the device of FIG. 1.
Figure 3:
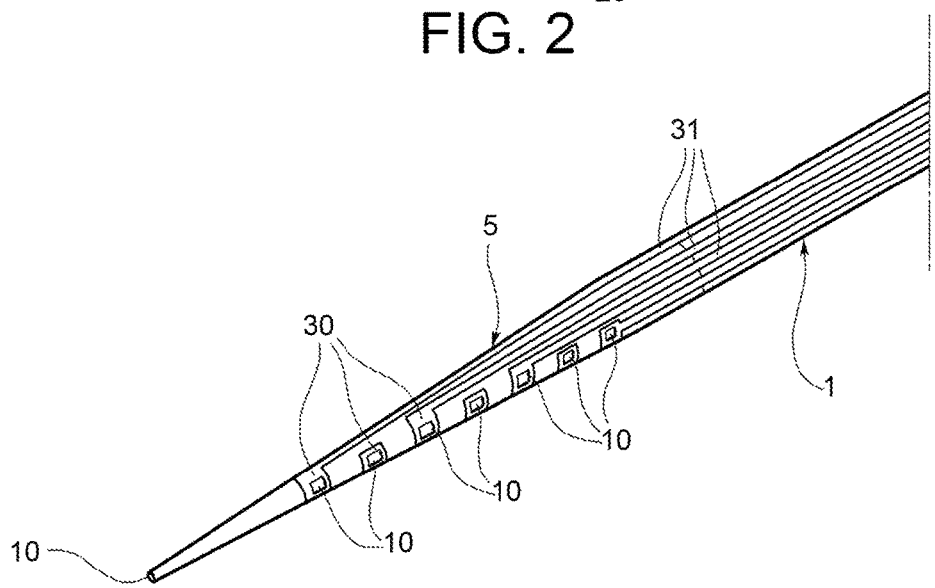
FIG. 3 is a perspective view illustrating a second embodiment of an optogenetic tool incorporating the device of FIG. 1.

The multi-point emitting single-fiber device 1 can he coupled to single or multiple recording systems with arbitrary geometries; an example is reported in FIG. 2, which shows a recording electrode array 20 supported by a shaft 21, and to support unit 23 providing, support to the single-fiber device 1 and shaft 21, and electrical connections to the electrode array 20. Single or multiple microwires, tetrodes and two-dimensional micromachined arrays similar to that proposed by Wang et al. can he integrated with the device according to the invention. In particular, after proper external insulation of the reflective coating deposited on the fiber's taper, a single microwire or tetrode can be placed close to each optical window and glued to the fiber, or electrical contacts consisting of independent metallic recording pads 30 (one per each optical window) and metallic paths 31 for external connection can he directly fabricated on the fiber itself (see for example FIG. 3). As a further option, the single fiber can be glued at the backside of linear arrays of recording sites (similar to the commercially available arrays from NeuroNexus) and through-holes can he milled in the silicon shall down to the back-connected tapered fiber close to the recording sites. These and further options for integrated multi-recording and multi-emitting optogenetic tools are possible given the versatility of the proposed optical system. It is even possible to address each recording site with a custom emitting point. Radiation wavelength, radiation pattern and light intensity can be tuned to obtain precise stimulation (or inhibition) of a small number of neurons neighbouring the recording site, while reducing direct illumination of the metallic pad itself.

Importantly, the optical windows can be engineered to obtain a uniform optical excitation of the brain region along the fiber taper 5. This allows the stimulation of a wider brain volume using a single optical fiber and without resorting to higher input, power, which otherwise can cause photoelectric artifacts and detrimental tissue heating. Moreover, proper engineering of the emission properties of each window to avoid direct illumination of the recording sites, together with reduced input power requirements, can strongly improve signal-to-noise ratio of the recorded electrical activity during optical stimulation by virtue of a reduced photoelectric noise. This allows the interrogation of broad neuronal networks while optically activating/inactivating specific sub-networks composed of smaller numbers of neurons. For example, it would be possible to record throughout all layers of the brain's neocortex while activating or inactivating specific layers.

A further advantage of the invention for multi-site stimulation lays in its compactness, which should minimize neuronal injury during insertion. Indeed the tapered fiber is designed to be sharp and smooth to avoid important tissue damages, but it is also stiff and straight enough for a correct insertion into the brain. Moreover, the integration of the tapered optical fiber with the electrical recording system implies that light sources and recording electrodes are bound together in a fixed relationship hence relative positions of excitation and recording, points are configure in advance and do not need to he inferred in a subsequent analysis.

A prototype of a multi-point emitting modal demodulator based on a tapered fiber has been developed and characterized in the laboratory. A multi-mode optical fiber (core diameter 50 µm, cladding diameter 125 µm, core refractive index $n_1$=464, cladding refractive index $n_2$=1.448, numerical aperture N.A.=0.22 taper angle between 1° and 10°, preferably between 3° and 6°, gold reflective coating thickness 300 nm, aperture on taper tip diameter 200 nm (see SEM micrographs in FIG. 4(a)), has been bought from Nanonics. To realize the optical windows, the optical fiber was inserted in a combined FIB/SEM (Focused Ion Beam/ScanningElectron Microscope) system, the FEI® Helios™ NanoLab™ 600i DualBeam™, equipped with the Tomahawk FIB column. For each window a 20 µm×20 µm area was scanned by the Ga+ ion. beam perpendicularly to the fiber axis (acceleration potential 30 keV, probe current 9.3 nA, dwell time 1 µs, process time 14 minutes), obtaining a milled depth of about 6 µm.

Figure 4:
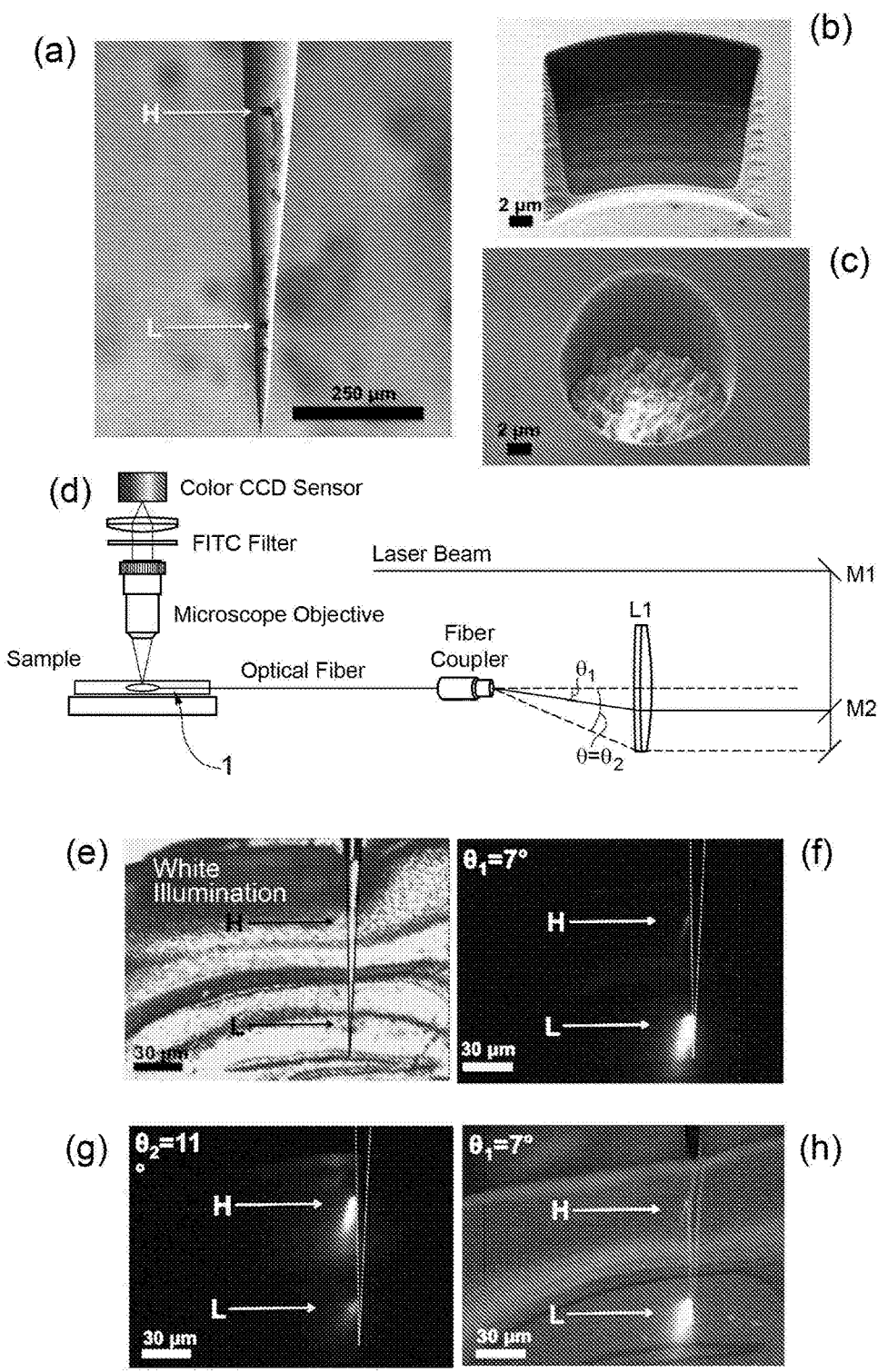
FIG. 4 shows: (a) a SEM bird-eye view of two optical windows on an optical fiber taper. The first and the second windows are 300 μm (L) and 900 μm (H) away from the fiber tip, respectively. (b, c) SEM micrograph of square (panel (b)) and circular (panel (c)) optical windows, milled perpendicularly to the fiber axis. (d) Optical setup used for an experiment. (e) White field image of a mouse coronal brain slice and the inserted optical fiber. The brain slice was marked with fluorescein. (f) Fluorescence image of the excited tissue region for $\theta=\theta_1=7°$. Guided light is emitted predominantly from the hole closer to the tip. (g) Fluorescence image of the excited tissue region for $\theta=\theta_2=11°$. Guided light is emitted predominantly from the hole farther from the up. (h) is the counter part of panel (d) obtained with a wide field illumination in order to assure the effective insertion of the fiber into the brain slice.

The two optical windows realized for this proof of concept, here after referred to as L, and H, were patterned 300 µm and 900 µm away from the taper tip 7, respectively (see FIG. 4(a)). Although the following discussion is focused on square windows (FIG. 4(b)), also other shapes can be realized by means of FIB milling (see, for instance, the circularly-shaped aperture displayed in FIG. 4(c)). As mentioned above, the fiber taper performs a selection of propagating and evanescent modes: the higher the order of the mode, the smaller its propagation length into the taper. Indeed, if the tip diameter is small enough, only the fundamental mode reaches the taper end, while all other modes became evanescent. As a consequence, high-order modes propagate on taper sections well away from the tip, while lower order modes are allowed to reach sections closer to the taper tip.

The modes injected into the core-cladding section of the fiber are controlled by means of a simple optical solution, based on tuning the input coupling angle θ at the distal end of the fiber, as displayed in FIG. 4(d). In its simplest form, the optical setup is composed by a fixed (M1) and a sliding (M2) mirror, whose position defines the input coupling angle θ (FIG. 4(d)). When the mirror M2 is in the Home position, the laser beam travels perpendicularly through the center of a plano-convex converging lens L1, which focuses the optical radiation coaxially to the optical fiber axis. If the mirror is instead moved along the optical axis, the focalization takes place with a different angle θ.

To test the effectiveness of the proposed device to dynamically deliver light in defined brain regions, the structured taper was inserted into 300 µm-thick mouse coronal brain slices, as shown in the bright field image displayed in FIG. 4(e). Brain slices were previously labelled with Fluorescein molecules (emission wavelength about 530 nm) and an excitation laser (wavelength ~473 nm) was coupled into the fiber at various θ.

The optical fiber of the experimental setup supports about 2163 modes, each of which has a propagation vector $k_j$, where j is the order of the mode. The propagation of the j-th mode into the waveguide is induced by the input-coupled angle θ. The efficiency at which each mode is excited into the fiber is proportional to the overlap integral between the j-th modal function and the input radiation. By modifying θ, the j-th overlap integral is modified, thus obtaining a light-intensity redistribution among the guided modes [Khilkvania, S. K., et al., Fiber and Integrated Optics 29, 62-75 (2009)], as follows. Assume the propagation vector as the sum of an axial and a transversal component, i.e. $k_j = k_{jT} + k_{jA}$. In general $k_{jT} \leq k_{(j+1)T}$, and the higher the order of the mode, the higher the ratio $k_{jT}/k_{jA}$. All excited modes propagate as far as the base of the tapered section, at which point their behavior is strongly modified, in terms of both real and imaginary part of the propagation constant. Indeed, the taper no longer supports all the modes excited into the optical fiber: the higher the order of the mode, the shorter the mode propagation distance into the taper. Moreover, $k_{jT}$ is a function of the position along the taper, and it increases as the waveguide diameter decreases.

Figure 5:
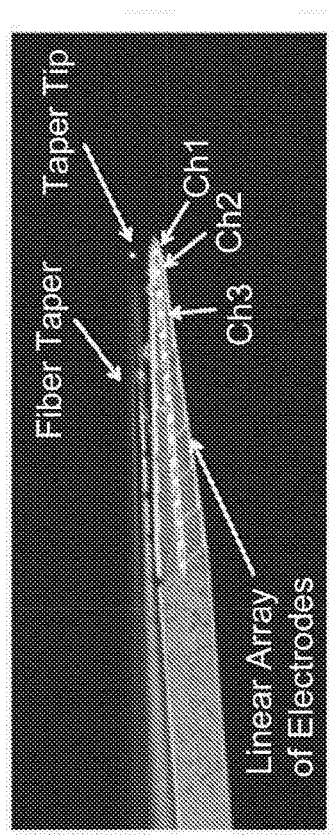
FIG. 5 shows: (a) an optical microscope image of an optrode realized according to the embodiment displayed in FIG. 2: the structured optical fiber is placed beside a linear array of electrodes designed for extracellular recording. Optical windows on the tapered fiber have been oriented to shine light in the region just above the recording pads. (b) Spike rate histogram for $\theta=3°$ obtained with the device reported in (a) implanted in a head-restrained transgenic mouse. (c) Spike-rate histogram for $\theta=8°$ obtained with the device reported in (a) implanted in a head-restrained transgenic mouse.
Figure 5:
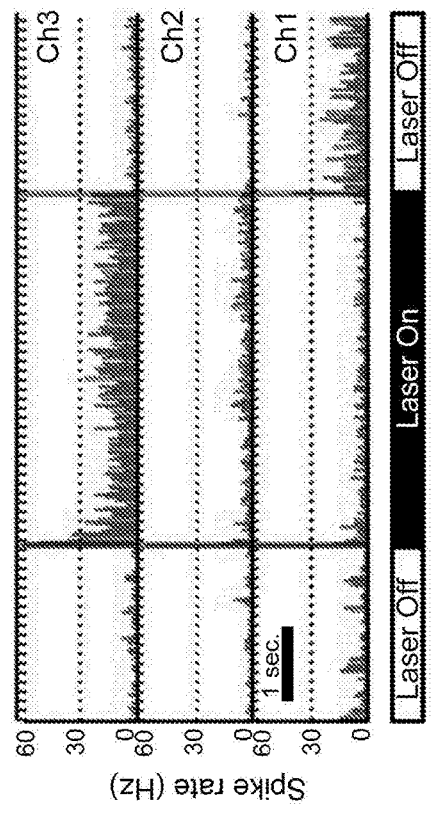
Figure 5:
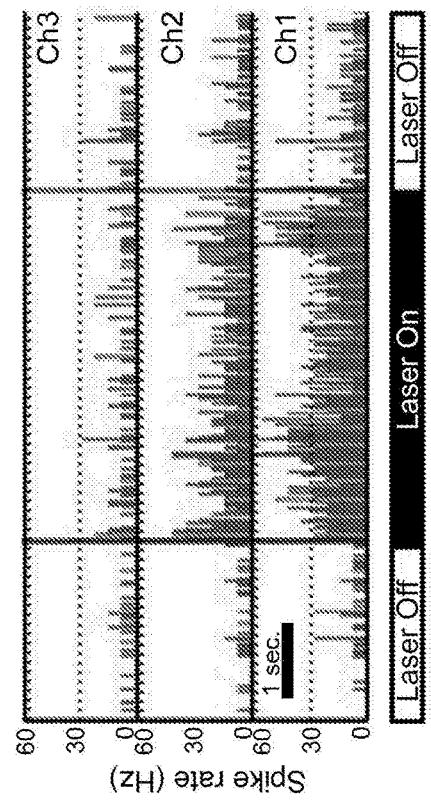

When $θ=θ_1=7°$, the excited modes reach the taper section at which the window L was realized with a $k_{jT}$ higher than that of the window H. As shown in FIG. 4(f), the injected modal subset is allowed to out-couple in the surrounding environment from the aperture L, while a negligible light leakage is observed from H. With increasing θ, the number of modes reaching L decreases, since higher-order modes are preferentially excited. However, higher-order modes mach high value of $k_{jT}$ for shorter propagation distances in the taper, so that the most of the light is out-coupled at window H, as demonstrated by the image reported in FIG. 4(g). in-vivo tests and implants have been performed by placing an array of electrodes for extracellular recording of neuronal signal beside a structured taper, as displayed in FIG. 5(a). In this case seven optical windows were opened all along the taper. This device was tested in-vivo in the brain of awake, head-restrained transgenic mice by inserting the fiber through a few millimeters-wide craniotomy. Sample results of the in-vivo tests are shown in FIG. 5(b,c): for θ=3° only electrodes placed close to the fiber tip (Ch1 and Ch2) detect photostimulated neuronal signal, whereas at θ=8° the photostimulated neuronal activity moves away from the tapered tip (on electrode Ch3).

Multi-wavelength emission has been also tested by using two different strategies. In the first strategy, lasers at different wavelengths were coupled at the distal end of the fiber at different input-coupling angles, thus allowing the out-coupling of specific wavelength at each optical window. In the second approach, a nanocomposite of PDMS/red-emitting colloidal nanoparticles (CdSeICdS dot-in-rod nanoparticles emitting at λ=620 nm) was prepared by dispersing colloidal nanoparticles in PDMS monomer at 8% wt concentration. The liquid-phase blend was drop-casted on throe of the optical windows and allowed to cure in air at room temperature for 24 hours. Blue-emitting, laser was coupled to the fiber and the emission properties were investigated by confocal imaging. Notably, by changing the fraction of blue incident light it is possible to tune the relative intensities of blue and rod radiation exiting the shielded windows. The intensity ratio can also be modified by changing the weight fraction of fluorescent dispersed nanoparticles.

Even though the proposed device has been at first conceived as a tool for optogenetics and optical modulation of neural state in research and medical fields, it can had further application in fundamental and applied physics research that relies on localized emission of light (optical tweezers, near-field optical microscopy, etc.), because multi-point emitting spots could be used to broaden the inspected areas or to increase the parallelization degree of their activity. Applications can be also envisioned in laser-assisted surgery.

Figure 6:
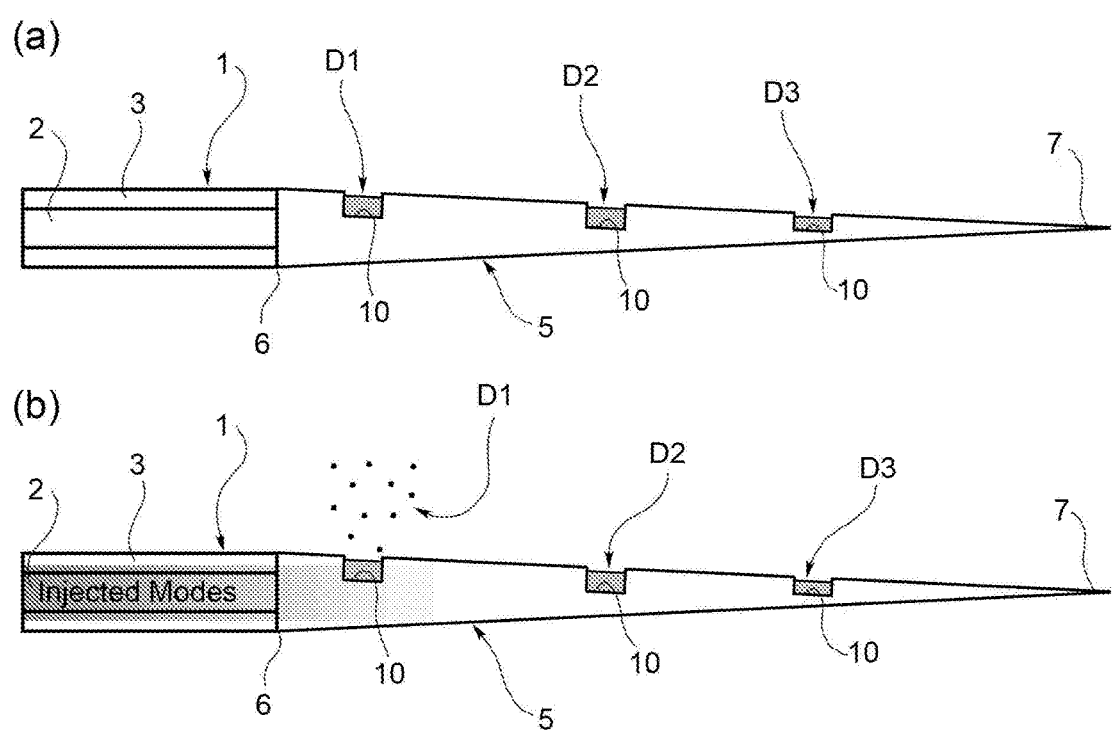
FIGS. 6(a) and 6(b) are schematic, cross-sectional views illustrating a drug delivery system incorporating the device of FIG. 1, shown in two different operating positions.

An example of application of the inventive device in a drug delivery technique is shown in FIGS. 6(a) and 6(b).

It is known that drugs for chronic or serious disease therapy may have dangerous side-effects. A conventional solution to this problem is to protect the human body from dangerous interactions with the drugs by enclosing them inside micro- or nano-capsules, until they can be released just in the tissue that must undergo the therapy. By realizing compounds based on drugs encapsulated in polymers or other materials that degrade when absorbing light, it has been demonstrated that drug-delivery can he triggered by optical radiation at both visible and infrared wavelengths. To this end, the proposed multi-point emitting device may he used as a carrier of optically deliverable drugs in order to reach specific biological tissues, such as deep brain regions and/or to match specific layers of the cerebral cortex. As already discussed, the device consists of a series of optical windows realized on the outer surface of a tapered optical fiber. Size and shape of the optical apertures can be engineered to facilitate their filling with one or more medical compounds D1, D2, D3, thus acting as drug reservoirs (see schematic representation in FIG. 6(a)). By virtue of the modal-demultiplexing principle, the light coupled into the fiber can pass through just one (or some) of the filled optical windows, thus enabling the delivery of the drugs just in one (or some) region(s) of the surrounding tissue, as schematically displayed in FIG. 6(b). It is worth mentioning that each window can be filled with a different drug and that the modal subsets injected at the distal end of the fiber can he chosen in order to custom distribute light intensity among the apertures. This allows the delivery dose for each of the drug to be tuned, thus allowing the possibility to design complex therapies based on different drugs released at different rates. Moreover, since compounds degrading at different wavelengths can be realized, each window can be filled with two or more drugs whose delivery can he controlled by modifying the wavelength of the light injected at the distal end of the fiber.

The invention claimed is:

1. A multi-point light-delivering device, comprising a waveguide carrying light along a longitudinal axis and including multiple optical windows, through which the carried light is out-coupled from the waveguide;
wherein said waveguide comprises a tapered region along which said optical windows are distributed, said tapered region comprising a tapered side surface, said multiple optical windows including a plurality of optical windows formed on said tapered side surface, wherein each optical window out-couples a specific subset of propagating modes of the carried light, to which said optical window is matched.

2. A device according to claim 1, wherein said multiple optical windows further include an optical window formed on a tip of the tapered region of the waveguide.

3. A device according to claim 1, wherein at least one of said optical windows is configured as a reservoir for containing a medical compound, said medical compound being optically deliverable by means of the light that is out-coupled by the optical window.

4. A device according to claim 1, wherein said waveguide is a single optical fiber.

5. A device according to claim 1, said device being provided for illuminating an optical sensitive material or environment, and being associated to an electrode array coupled to the waveguide for recording electric signals from the illuminated material or environment.

6. A device according to claim 5, wherein said electrode array is arranged on said tapered side surface of said tapered region.

7. A device according to claim 1, wherein said device is a neuronal interface tool implantable in a neuronal tissue.

8. A device according to claim 1, wherein said device is an optogenetic device implantable in a tissue or biological system sensible to light.

9. A device according to claim 1, wherein said device is a device for endoscopy or laser-based surgery.

10. A device according to claim 1, wherein said tapered region has a taper angle between 1° and 10°.

11. A device according to claim 10, wherein said tapered region has a taper angle between 3° and 6°.

12. A multi-point light-delivering device, comprising a waveguide carrying light along a longitudinal axis and including multiple optical windows, through which the carried light is out-coupled from the waveguide;
wherein said waveguide comprises a tapered region along which said optical windows are distributed, said tapered region comprising a tapered side surface and a tip, said optical windows including at least one optical window formed on said tapered side surface and a single optical window formed on said tip, wherein each optical window out-couples a specific subset of propagating modes of the carried light, to which said optical window is matched.

* * * * *

UNITED STATES PATENT AND TRADEMARK OFFICE
CERTIFICATE OF CORRECTION

PATENT NO. : 10,398,293 B2
APPLICATION NO. : 14/905374
DATED : September 3, 2019
INVENTOR(S) : Ferruccio Pisanello et al.

Page 1 of 1

It is certified that error appears in the above-identified patent and that said Letters Patent is hereby corrected as shown below:

-(71) The first applicant reads:
FONDAZIONE INSTITUTO ITALIANO DI TECHNOLOGIA

-(71) The first applicant should read:
FONDAZIONE ISTITUTO ITALIANO DI TECHNOLOGIA Signed and Sealed this
Twenty-ninth Day of October, 2019

Andrei Iancu
*Director of the United States Patent and Trademark Office*

UNITED STATES PATENT AND TRADEMARK OFFICE
CERTIFICATE OF CORRECTION

PATENT NO.           : 10,398,293 B2
APPLICATION NO.   : 14/905374
DATED               : September 3, 2019
INVENTOR(S)       : Ferruccio Pisanello et al.

It is certified that error appears in the above-identified patent and that said Letters Patent is hereby corrected as shown below:

-(71) The first applicant reads:
FONDAZIONE INSTITUTO ITALIANO DI TECHNOLOGIA

-Should read:
FONDAZIONE ISTITUTO ITALIANO DI TECNOLOGIA

This certificate supersedes the Certificate of Correction issued October 29, 2019.

Signed and Sealed this
Twenty-sixth Day of May, 2020

Andrei Iancu
*Director of the United States Patent and Trademark Office*